United States Patent [19]

Braca et al.

[11] Patent Number: 4,780,566

[45] Date of Patent: Oct. 25, 1988

[54] PROCESS FOR PRODUCING ETHYL ACETATE BY HOMOLOGATION OF METHYL ACETATE

[75] Inventors: Giuseppe Braca; Glauco Sbrana, both of Pisa; Anna Maria Raspolli, Putignano; Franco Zanni, Pisa, all of Italy

[73] Assignee: Consiglio Nazionale Delle Ricerche, Rome, Italy

[21] Appl. No.: 587,632

[22] Filed: Mar. 8, 1984

[30] Foreign Application Priority Data

Jun. 15, 1983 [IT] Italy .............................. 21645 A/83

[51] Int. Cl.$^4$ ...................... C07C 67/02; C07C 67/36
[52] U.S. Cl. ..................................... 560/265; 560/232
[58] Field of Search ............................... 560/265, 232

[56] References Cited

U.S. PATENT DOCUMENTS 4,189,441  2/1980  Braca et al. ..................... 560/265
4,371,724  2/1983  Lin ................................. 560/265

FOREIGN PATENT DOCUMENTS 0031606   7/1981  European Pat. Off. .
0063105  10/1982  European Pat. Off. .

Primary Examiner—Werren B. Lone
Attorney, Agent, or Firm—Stevens, Davis, Miller & Mosher

[57] ABSTRACT

A process is described for producing ethyl acetate either alone or in mixture with acetic acid, by homologation of methyl acetate with CO and $H_2$ in the presence of a catalyst in the form of a Ru compound and a catalysis promoter of hard acid type.

The process has considerable advantages over known processes, in particular with regard to the reaction rate and the low formation of undesirable by-products.

1 Claim, No Drawings

PROCESS FOR PRODUCING ETHYL ACETATE BY HOMOLOGATION OF METHYL ACETATE

This invention relates to a new process for producing ethyl acetate alone or in mixture with acetic acid, starting from methyl acetate or a methyl acetate-acetic acid mixture, by homologation with CO and $H_2$ in the presence of a ruthenium catalyst.

A previous patent (G. Braca et al.—U.S. Pat. No. 4,189,441 of 1980) describes a process for preparing ethyl acetate from methyl acetate and/or dimethyl ether by reacting CO and $H_2$ in the presence of a catalytic system comprising a ruthenium carbonyl compound and an iodized or brominated promoter in the form of a halogen acid, an alkyl halide or an ionic inorganic halide.

This process has certain applicational limitations, particularly when methyl acetate is used as the starting substance. The limitations are due essentially to low catalytic activity and limited ethyl acetate and acetic acid selectivity (max. 50-60% at high methyl acetate conversion).

There is also the formation of considerable quantities of hydrocarbons, which are unrecoverable are therefore undesirable, products derived from ester hydrolysis, and high molecular weight by-products derived from the carbonylation and homologation of the ethyl derivatives.

These products, which increase in quantity as the conversion increases, all contribute to lower the selectivity of the process and complicate the subsequent separation of the reaction products.

An ethyl acetate production process is also known which utilizes the same process but uses a more complicated catalytic system (European patent application No. 31784/1981) constituted by a mixed cobalt and ruthenium system in the presence of two different iodized promoters (one being an alkyl iodide and the other an ionic mineral, ammonium or phosphonium iodide).

The complexity of this catalytic system constitutes a considerable economical disadvantage and creates difficulty in recycling the catalyst, without producing any considerable improvement in activity. In addition, the reaction by-products include acetaldehyde, a compound which can undergo aldol condensation with the formation of high-boiling products.

Another known patent (European patent application No. 31606/1981) describes a process for producing acetic acid and ethyl acetate from methyl acetate by a very costly catalytic system comprising a ruthenium compound, a compound of another group VIII metal (Rh or Pd) and an iodide or bromide of a group II metal or of a transition metal, and an organic binder. This costly catalytic system in reality shows low activity, and moreover provides low selectivity of ethyl acetate, which is obtained only in the molar ratio of 1:2 with respect to the acetic acid. The object of the present invention is to propose a new process for the homologation of methyl acetate to ethyl acetate which enables either ethyl acetate to be obtained alone or mixtures of ethyl acetate and acetic acid to be obtained with a high acetate content, using methyl acetate or mixtures of methyl acetate and acetic acid as the starting substance, to produce results which are decidedly superior in all aspects to those results obtainable with processes of the prior art.

The new process for preparing ethyl acetate consists essentially of reacting methyl acetate, either alone or in solution with acetic acid, and carbon monoxide and hydrogen at a temperature of between 150° and 250° C. and a pressure of between 100 and 200 atm., in the presence of a ruthenium catalyst and a promoter.

The promoters used according to the present invention pertain essentially to the following classes of compound:

A—Actual Lewis acids such as the halides of metals of group II, III, IV and V of the periodic system, and preferably $AlCl_3$, $AlBr_3$, $AlI_3$, $TiI_3$, $TiCl_3$, $TiI_4$, $Ti(OAc)_3$, $ZnI_2$, $SbCl_5$, $AsCl_3$ and the like;

B—Strong non-hydrogen halide acids which are incapable of entering the coordination sphere of the metal and thus non-complexing, such as $HBF_4$, $HPF_6$ and the like;

C—Metal ions derived preferably from alkaline or alkaline-earth salts, preferably $Li^+$, $Na^+$, $K^+$, $Be^{2+}$, $Ca^{2+}$, $Mg^{2+}$, or from trivalent metal salts such as $Al^{+3}$, $Ti^{+3}$, and the like. These metal ions must be used in the presence of organic compounds having sequential $-O-CH_2-CH_2-$ groups such as the macrocyclic ethers or crown ethers and their open-chain analogues, which function as complexing agents.

When a promoter chosen from the aforesaid classes does not contain iodine is used, an iodized compound essentially in the form of an alkyl iodide or an inorganic iodide must be added to the system. The use of potassium iodide has been found particularly interesting, as its use leads to a higher reaction rate and improved selectivity, while at the same time making the reaction environment less corrosive.

The Ru compounds which can be used in the catalytic system according to the present invention are carbonyl derivatives of Ru, such as $Ru_3(CO)_{12}$, $Ru(CO)_4I_2$, $Ru(CO)_3Cl_2$ and the like, or Ru compounds which under the reaction conditions form Ru carbonyls, such as Ru-acetylacetonate, Ru salts of carboxylic acids, sodium hexachlororuthenate, ruthenium triiodide and the like.

The components of the catalytic system are mixed in the following molar ratios:

Ru compound/promoter/iodized compound from 1/5/5 to 1/25/10.

The crown ether or the open-chain polyether is added in a molar ratio of 0.2 to 2 with respect to metal ions (Group C), and in general remains unaltered during the reaction and can be easily recycled together with the ruthenium catalyst and the metal promoter.

The reaction is carried out at a temperature of between 150° and 250° C., and a temperature at the lower end of the range can advantageously be used as the catalytic system is much more active than traditional ones. However, to obtain a high reaction rate together with high ethyl acetate and acetic acid selectivity, the preferred temperature is between 180° and 200° C.

The CO/$H_2$ mixture when fed into the reaction compartment must ensure a partial CO pressure sufficient to prevent the ruthenium carbonly derivative decomposing to metal ruthenium. In all cases, the total pressure must be at least 50 atm., and preferably 100-200 atm.

The $H_2$/CO ratio in the gaseous reaction mixture can vary between 0.1 and 10, the preferred ratio being between 0.5 and 2.5.

As stated above, the new process enables numerous advantages to be obtained compared with the processes of the prior art.

Firstly, there is a significant increase in the catalytic activity of the system. In some cases, in the presence of the promoter, the conversion obtained is double that which is obtained in its absence.

Again, even at high conversion (greater than 80%) the ethyl acetate and acetic acid selectivity is always greater than 70%, and under optimum conditions selectivity exceeds 90%, and the amount of hydrolysis products remains low. At the same time, smaller quantities of higher homologues and carbonylation products are produced than obtained for equal conversions in tests carried out in the absence of acid promoters.

One of the most significant advantages of the new catalytic system is that even at a conversion of around 80%, the selectivity in terms of hydrocarbon products remains very low, and much lower than that obtained in all known processes.

Finally, it should be noted that the new catalytic system enables the reaction to be orientated prevalently towards the formation of ethyl acetate, so that when this is formed in combination with acetic acid the molar ratio of ethyl acetate:acetic acid generally lies between 1 and 2.

The new process according to the present invention can be accomplished in a manner similar to the other homologation processes, even when starting from dimethyl ether. However, when this starting substance is used, the advantageous aspects heretofore described for methyl acetate with respect to processes of the known art are surprisingly not obtained.

In order to make the process according to the present invention more easily reproducible and to better illustrate the advantages obtainable by its application, some embodiments are described hereinafter by way of non-limiting examples.

In all examples the selectivity in terms of the various products has been calculated using the following equation:

$$\text{Selectivity} = \frac{\text{moles product} \times \text{No. of methyl groups}}{\Sigma \text{ moles recovered product} \times \text{No. methyl groups}} \times 100$$

Water and $CO_2$ are not considered, and ethane is considered as a product with a single methyl.

EXAMPLE 1

0.36 mmoles of $Ru(Acac)_3$, 3.6 mmoles of $AlI_3$, 0.18 moles of methyl acetate (15 ml) and 0.18 moles of acetic acid (10.5 ml) are fed into a Hastelloy C autoclave having capacity of 150 ml. A $CO/H_2$ mixture of molar ratio ½ is compressed into the autoclave until the pressure reaches 150 atm.

The autoclave is then placed in a bath temperature-controlled at 200° C. and is kept under agitation for 10 hours.

After the autoclave has been cooled, the product liquid mixture (26 g) and gaseous mixture (18.8 Nl) are discharged and analysed by gas chromatography.

The process data and the results obtained are shown in Table 1.

A methyl acetate conversion of 57% was obtained, with the following selectivities:

| | |
|---|---|
| ethyl acetate | 43.5% |
| acetic acid | 37.8% |
| alcohols and ethers | 5.3% |
| $CH_3 + C_2H_6$ | 13.4% |
| higher products | traces |

EXAMPLES 2–6

Table 1 shows other homologation tests carried out by the same procedure described in Example 1, except that the type of promoter is varied.

EXAMPLES 7–8

Table 1 shows further homologation tests carried out by the same operational procedure described in Example 1, except that initially a crown ether or an open-chain polyether (tetraethyleneglycoldimethylether, TEGDME) is added to the system.

EXAMPLE 9

A comparison test was carried out by the procedure described in U.S. Pat. No. 4,189,441, using the same autoclave as in the preceding examples and a reaction mixture constituted by 0.18 moles of methyl acetate and 0.18 moles of acetic acid. The operating conditions were the same as described above.

In this case however a catalytic system was used in the form of $Ru(Acac)_3$ (0.36 mmoles) with $CH_3I$ (3.6 mmoles) as promoter.

The following results were obtained:

| | | |
|---|---|---|
| methyl acetate conversion | 35.6% | |
| product selectivity: | | |
| ethyl acetate | 65.5% | |
| acetic acid | — | more selective towards ester |
| alcohols and ethers | 13.8% | |
| higher products | traces | |
| $CH_4 + C_2H_6$ | 19.6% | |

The liquid product fraction also contained 4.1% of water.

The results are shown in Table 1.

EXAMPLE 10

A comparison test was carried out operating exactly as described in Examples 7–8, but without adding crown ether or TEGDME. The results are shown in Table 1.

TABLE 1

| Ex. No. | promoter mmoles | Iodized compound mmoles | Polyether mmoles | AcOMe convers. % | AcOH convers. % | Selectivity % | | | | | |
|---|---|---|---|---|---|---|---|---|---|---|---|
| | | | | | | AcOEt | AcOH | Et. Alc. | Propyl derivat. | Methane + ethane | AcOet + AcOH |
| 1 | $AlI_3$ (3.6) | — | — | 57.0 | — | 43.5 | 37.8 | 5.3 | traces | 13.4 | 81.3 |
| 2 | $TiI_4$ (1.1) | — | — | 43.3 | 3.7 | 68.8 | — | 13.3 | " | 17.8 | 68.8 |
| 3 | $ZnI_2$ (1.8) | — | — | 17.8 | 3.9 | 70.3 | — | 11.4 | " | 18.3 | 70.3 |

TABLE 1-continued

| Ex. No. | promoter mmoles | Iodized compound mmoles | Polyether mmoles | AcOMe convers. % | AcOH convers. % | Selectivity % | | | | | |
|---|---|---|---|---|---|---|---|---|---|---|---|
| | | | | | | AcOEt | AcOH | Et. Alc. | Propyl derivat. | Methane + ethane | AcOet + AcOH |
| 4 | HBF$_4$ (3.6) | CH$_3$I (3.6) | — | 41.5 | — | 60.0 | 11.5 | 10.9 | " | 17.6 | 71.5 |
| 5 | HPF$_6$ (3.6) | KI (3.6) | — | 32.0 | — | 38.7 | 48.1 | 1.8 | " | 11.4 | 86.8 |
| 6 | Ti(OAc)$_3$ (3.6) | CH$_3$I (3.6) | — | 51.1 | — | 70.6 | 2.4 | 7.6 | 3.6 | 16.8 | 73.0 |
| 7 | K$^+$ (3.6) | — | 18-crown-6 (4.5) | 58.5 | — | 53.7 | 36.8 | 1.5 | traces | 7.8 | 90.5 |
| 8 | K$^+$ (3.6) | — | TEGDME (5.4) | 42.2 | — | 42.2 | 44.0 | 2.1 | " | 11.7 | 86.2 |
| 9 | — | CH$_3$I (3.6) | — | 35.6 | 19.1 | 65.5 | | 5.3 | " | 19.6 | 65.5 |
| 10 | — | KI | — | 35.9 | — | 51.3 | 28.8 | 2.1 | " | 17.7 | 80.1 |

Homologation tests with the promoters were also repeated in a 1 liter Hastelloy C reactor fitted with a magnetic agitator and provided with devices for withdrawing liquid and gas samples. This enabled the conversion of reactants to product and the variation in the liquid and gas product composition to be followed with time.

The results obtained in the tests carried out with this apparatus using the new promoters (Examples 11, 12, 13) were also compared with the results obtained in tests carried out under the same conditions with catalytic systems of known type (Examples 14, 15) not containing the promoter of this invention.

EXAMPLE 11

1.438 g of Ru(Acac)$_3$ (3.6 mmoles), 5.98 g of KI (36 mmoles), 8 g of a 60% aqueous solution of HPF$_6$ (36 mmoles), 133 g (1.8 moles) of methyl acetate and 108 g (1.8 moles) of acetic acid were fed into a Hastelloy C reactor of capacity 1 liter fitted with an efficient agitation system and a rotating magnetic coupling, and provided with devices for withdrawing liquid and gaseous samples.

A CO/H$_2$ (ratio ½) mixture was then compressed into the autoclave until a pressure of 120 atm. was obtained.

The reactor was then heated to a temperature of 200° C. while maintaining the pressure constant at a value of 160±5 atm. by feeding CO/H$_2$ (ratio 1/1) from a high pressure reservoir.

The reaction was continued for 24 hours, and the variation in the liquid and gaseous product composition with time was followed by withdrawing and analysing samples at various times. The conversion and selectivity data at various times are shown in Table 2.

After 24 hours the reactor was rapidly cooled, and the liquid and gaseous products were discharged and analysed by gas chromatography.

The methyl acetate conversion was 75% and the various product selectivities were as follows:

| | |
|---|---|
| ethyl acetate | 46.2% |
| acetic acid | 36.4% |
| alcohols + ethers | 2.2% |
| propyl and propionic derivatives | 2.6% |
| CH$_4$ + C$_2$H$_6$ | 12.0% |

TABLE 2

| | CATALYTIC SYSTEMS WITH HARD ACID PROMOTERS | | | | | | CATALYTIC SYSTEMS WITHOUT ACID PROMOTERS (comparison) | | | |
|---|---|---|---|---|---|---|---|---|---|---|
| Example No. | 11 | | 12 | | 13 | | 14 | | 15 | |
| Ruthenium compound (mmoles) | Ru(Acac)$_3$ (3.6) | | Ru(Acac)$_3$ (3.6) | | Ru(Acac)$_3$ (3.6) | | Ru(Acac)$_3$ (3.6) | | Ru(Acac)$_3$ (3.6) | |
| Iodized compound (mmoles) | KI (36) | | — | | — | | CH$_3$I (36) | | KI (36) | |
| promoter (mmoles) | HPF$_6$ (36) | | AlI$_3$ (18) | | KI/TEGDME (36)/(54) | | — | | — | |
| Time | 8 h | 24 h | 4 h | 8 h | 4 h | 24 h | 8 h | 26 h | 8 h | 24 h |
| Conversion % | 49.7 | 75.0 | 50.6 | 77.5 | 42.4 | 75 | 53.5 | 84.6 | 61.0 | 81.8 |
| Selectivity % | | | | | | | | | | |
| Alcohols + ethers | 2.1 | 2.2 | 6.8 | 5.0 | 0.7 | 0.8 | 8.8 | 8.7 | 0.4 | 0.3 |
| Ethyl acetate | 43.3 | 46.2 | 42.8 | 40.7 | 43.3 | 29.8 | 61.9 | 51.8 | 21.1 | 23.1 |
| Acetic acid | 43.8 | 36.4 | 35.1 | 33.3 | 47 | 56.5 | 6.7 | 3.1 | 63.8 | 58.1 |
| Propionates and n-propyl deriv. | 0.7 | 2.6 | traces | 8.3 | traces | 1.7 | 4.0 | 12.0 | traces | traces |
| Methane + ethane | 8.6 | 12.0 | 15.3 | 12.7 | 9 | 11.2 | 18.6 | 24.4 | 14.6 | 18.5 |
| Water % by weight | 3.4 | 5.7 | 4.7 | 7.7 | 0.9 | 1.0 | 5.0 | 5.6 | 1.3 | 3.6 |

An analysis of the data given in Table 1 shows that considerably higher methyl acetate conversions can be obtained with the new promoters for equal conditions.

In addition, the ethyl acetate and acetic acid selectivity is always very high, and can exceed 90%. At the same time, the production of by-products and in particular methane and ethane which constitute the greatest loss in the process falls from about 20% to a value which can be contained at around 10% or even less.

An analysis of the results given in Table 2 shows that the new catalytic systems are extremely more active than known systems.

In this respect, it is possible in only 8 hours to obtain a methyl acetate conversion which with known systems is obtained only in a time of 24 hours. Moreover, for equal times, the ethyl acetate and acetic acid selectivity is considerably higher and the production of methane and ethane and of propyl derivatives is considerably lower.

What is claimed is:

1. A process for preparing ethyl acetate by homologation of methyl acetate with CO and $H_2$, wherein the reaction is carried out in the presence of a catalyst system comprising:

a ruthenium carbonyl compound or a compound which forms a ruthenium carbonyl compound under reaction conditions; and a promoter consisting of KI in the presence of crown ethers or open chain chain polyethers containing —$CH_2CH_2O$-units wherein said ether is present in a molar ratio of between 0.2 and 2 moles per gram atom of KI.

* * * * *